United States Patent [19]

Nestor et al.

[11] Patent Number: 4,900,933

[45] Date of Patent: Feb. 13, 1990

[54] EXCITATION AND DETECTION APPARATUS FOR REMOTE SENSOR CONNECTED BY OPTICAL FIBER

[75] Inventors: James R. Nestor, Northboro; Jonathan D. Schiff, Billerica; Benjamin H. Priest, Bolton, all of Mass.

[73] Assignee: C. R. Bard, Inc., Murray Hill, N.J.

[21] Appl. No.: 28,198

[22] Filed: Mar. 20, 1987

Related U.S. Application Data

[63] Continuation-in-part of Ser. No. 904,963, Sep. 8, 1986, Pat. No. 4,861,727.

[51] Int. Cl.$^4$ ............................................. G01N 21/64
[52] U.S. Cl. ............................. 250/458.1; 250/252.1; 250/461.2; 356/41
[58] Field of Search ............... 250/458.1, 461.1, 461.2, 250/252.1, 354.1; 356/41

[56] References Cited

U.S. PATENT DOCUMENTS

| | | | |
|---|---|---|---|
| Re. 31,879 | 5/1985 | Lubbers et al. | 436/133 |
| 3,612,866 | 10/1971 | Stevens | 250/71 |
| 3,647,299 | 3/1972 | Lavallee | 356/41 |
| 3,804,535 | 4/1974 | Rodriguez | 356/217 |
| 3,847,483 | 11/1974 | Shaw et al. | 356/41 |
| 3,891,853 | 6/1975 | Kremen et al. | 250/458.1 |
| 3,971,941 | 7/1976 | Sewell et al. | 250/330 |
| 4,006,360 | 2/1977 | Mueller | 250/461.2 |
| 4,058,732 | 11/1977 | Wieder | 250/461.1 |
| 4,075,493 | 2/1978 | Wickersheim | 250/461 R |
| 4,167,331 | 9/1979 | Nielsen | 356/39 |
| 4,178,917 | 12/1979 | Shapiro | 128/665 |
| 4,266,554 | 5/1981 | Hamaguri | 128/633 |
| 4,313,344 | 2/1982 | Brogardh et al. | 73/355 R |
| 4,365,153 | 12/1982 | Seigel et al. | 250/461.1 |
| 4,437,772 | 3/1984 | Samulski | 374/129 |
| 4,446,871 | 5/1984 | Imura | 128/633 |
| 4,447,546 | 5/1984 | Hirschfeld | 250/227 |
| 4,448,547 | 5/1984 | Wickersheim | 374/131 |
| 4,453,218 | 6/1984 | Sperinde et al. | 364/416 |
| 4,459,044 | 7/1984 | Alves | 374/131 |
| 4,476,870 | 10/1984 | Peterson et al. | 128/634 |
| 4,523,279 | 6/1985 | Sperinde et al. | 364/416 |
| 4,558,014 | 12/1985 | Hirschfeld et al. | 250/227 |
| 4,560,286 | 12/1985 | Wickersheim | 374/131 |
| 4,575,259 | 3/1986 | Bacci et al. | 374/130 |
| 4,576,173 | 3/1986 | Parker et al. | 128/633 |
| 4,586,513 | 5/1986 | Hamaguri | 128/633 |
| 4,592,361 | 6/1986 | Parker et al. | 128/633 |
| 4,598,715 | 7/1986 | Machler et al. | 128/634 |
| 4,621,643 | 11/1986 | New, Jr. et al. | 128/633 |
| 4,622,468 | 11/1986 | Stefanski et al. | 250/458.1 |
| 4,623,248 | 11/1986 | Sperinde | 356/41 |
| 4,644,154 | 2/1987 | Brogårdh | 250/227 |
| 4,651,741 | 3/1987 | Passafaro | 128/633 |
| 4,652,143 | 3/1987 | Wickersheim et al. | 374/161 |
| 4,661,711 | 4/1987 | Harjunmaa | 250/459.1 |
| 4,681,444 | 7/1987 | Ferber et al. | 356/318 |
| 4,792,689 | 12/1988 | Peterson | 250/458.1 |

OTHER PUBLICATIONS

John I. Peterson et al, "Fiber-Optic Probe for in Vivo Measurement of Oxygen Partial Pressure," *Analytical Chemistry*, vol. 56, No. 1, Jan., 1984, pp. 62–66.

Photonics Spectra, Mar. 1984, pp. 54–59.

L. Jerome Krovetz et al, "Application of an Improved Intracardiac Fibreoptic System," *British Heart Journal*, 1978, vol. 40, pp. 110–113.

Bruce J. Tromberg et al, "Optical Fiber Fluoroprobes for Biological Measurements," *Applied Spectroscopy*, vol. 38, No. 1, 1984, pp. 38–42.

Brochure describing the Bentley Gas-Stat monitoring system; undated.

*Primary Examiner*—Carolyn E. Fields
*Attorney, Agent, or Firm*—Wolf, Greenfield & Sacks

[57] ABSTRACT

Sensing apparatus for remote sensing of quantities such as blood oxygen concentration using a phosphorescent material located at one end of an optical fiber. The phosphorescent material emits a relatively long-lived luminescence when exposed to energy in a predetermined wavelength range. The sensing apparatus includes a light source for generating an incident pulsed energy signal within the predetermined wavelength range and a detector subsystem for selectively detecting the long-lived luminescence from the phosphorescent material. The light source and the detector subsystem are coupled to the other end of the optical fiber along a common optical path. The detector subsystem includes dual channels for detecting a measuring wavelength and a reference wavelength in the long-lived luminescence. The detector subsystem is inhibited during the incident pulsed energy signal to provide low noise operation. The detected signals are integrated and averaged to improve accuracy. A calibration source is provided for calibrating the detection subsystem.

17 Claims, 6 Drawing Sheets

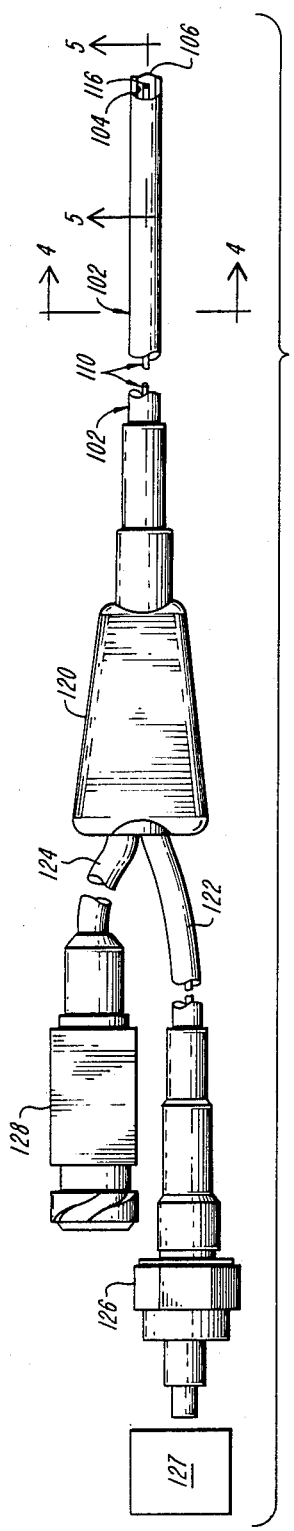
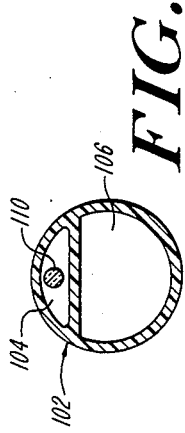
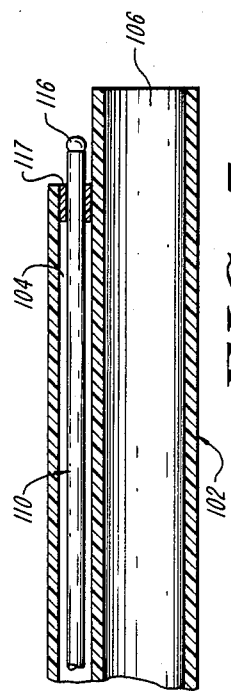
FIG. 3
FIG. 4
FIG. 5

EXCITATION AND DETECTION APPARATUS FOR REMOTE SENSOR CONNECTED BY OPTICAL FIBER

CROSS REFERENCE TO RELATED APPLICATIONS

This application is a continuation-in-part of copending application Ser. No. 904,963 filed Sept. 8, 1986, now U.S. Pat. No. 4,861,727.

FIELD OF THE INVENTION

This invention relates to an excitation and detection apparatus for use with a sensor remotely located at the end of an optical fiber and, more particularly, to an excitation and detection apparatus which transmits an incident pulsed energy signal to the sensor and detects relatively long-lived luminescence generated by the sensor.

BACKGROUND OF THE INVENTION

A blood gas analysis is performed on many hospital patients both during and after surgery. The three parameters of interest are the partial pressures of oxygen ($PO_2$) and carbon dioxide ($PCO_2$), and the negative logarithm of hydrogen ion activity, the pH. These three parameters give a good indication of a patient's cardiac, respiratory and circulatory functioning, and the rate of metabolism. Monitoring the level of oxygen gas in the blood is important for determining the amount of oxygen being delivered to the tissues.

Several sophisticated blood gas analyzers are commercially available for analyzing blood samples after the blood is extracted from the patient (in vitro). However, the withdrawal and subsequent analysis of a blood sample is both cumbersome and time-consuming and does not permit continuous monitoring of the dissolved gases in a patient's blood. There has been a need for many years for a system which would enable blood gas measurements to be made directly in the patient (in vivo), thereby avoiding the difficulties and expense inherent in the in vitro techniques.

Among the suggestions in the prior art was the use of indwelling electrode probes for continuous monitoring of the blood gas. The in vivo electrode probes have not been generally acceptable. Two principal disadvantages of electrode probes are the danger of using electrical currents in the body and the difficulty of properly calibrating the electrodes.

Also among the suggested techniques for in vivo measurement has been the use of fiber optic systems. In a fiber optic system, light from a suitable source travels along an optically conducting fiber to its distal end where it undergoes some change caused by interaction with a component of the medium in which the probe is inserted or interaction with a material contained in the probe tip which is sensitive to (i.e., modified by) a component in the medium. The modified light returns along the same or another fiber to a light-measuring instrument which interprets the return light signal.

Fiber optic sensors appear to offer several potential benefits. A fiber optic sensor is safe, involving no electrical currents in the body. Optical fibers are very small and flexible, allowing placement in the very small blood vessels of the heart. The materials used, i.e., plastic, metal, and glass, are suitable for long-term implantation. With fiber optic sensing, existing optical measurement techniques could be adapted to provide a highly localized measurement. Light intensity measurements could be processed for direct readout by standard analogue and digital circuitry or a microprocessor. However, although the potential benefits of an indwelling fiber optic sensor have long been recognized, they have not yet been realized in widely accepted commercial products. Among the principal difficulties has been in the development of a sensor in a sufficiently small size which is capable of relatively simple and economical manufacture so that it may be disposable.

An oxygen sensor based on oxygen-quenched fluorescence is described in U.S. Pat. No. Re. 31,879 to Lübbers et al. Lübbers et al. describe an optode consisting of a light-transmissive upper layer coupled to a light source, an oxygen-permeable lower diffusion membrane in contact with an oxygen-containing fluid, and a middle layer of an oxygen-quenchable fluorescent indicating substance such as pyrenebutyric acid. When illuminated by a source light beam of a predetermined wavelength, the indicating substance emits a fluorescent beam of a wavelength different from the source beam and whose intensity is inversely proportional to the concentration of oxygen present. The resultant beam emanating from the optode, which includes both a portion of the source beam reflected from the optode and the fluorescent beam emitted by the indicating substance, is discriminated by means of a filter so that only the fluorescent beam is sent to the detector. In a second embodiment, the optode consists of a supporting foil made of a gas-diffusable material such as silicone in which the fluorescent indicating substance is randomly mixed, preferably in a polymerization type reaction, so that the indicating substance will not be washed away by the flow of blood over the optode. Lübbers et al. assert that both optodes can be adapted for in vivo use by disposing the same at the distal end of a catheter containing a pair of optical fibers for the incident and outgoing beams. However, the multi-layer optode of the first embodiment would be difficult to miniaturize. Lübbers et al. fails to disclose any method for attaching the alternative supporting foil to the distal end of the optical fibers or catheter. Furthermore, these sensors require at least two optical fibers which further limits miniaturization of the device.

Another $PO_2$ sensor probe utilizing an oxygen-sensitive fluorescent intermediate reagent is described in U.S. Pat. No. 4,476,870 to Peterson et al. The Peterson et al. probe includes two optical fibers ending in a jacket of porous polymer tubing. The tubing is packed with a fluorescent light-excitable dye adsorbed on a particulate polymeric support. The polymeric adsorbent is said to avoid the problem of humidity sensitivity found with inorganic adsorbents such as silica gel. The probe is calibrated by using a blue light illuminating signal and measuring both the intensity of the emitted fluorescent green signal and the intensity of the scattered blue illuminating signal. Again, it is difficult to miniaturize the Peterson et al. sensor tip wherein a porous particulate polymer is packed within an outer tubing.

U.S. Pat. No. 3,612,866 to Stevens describes another method of calibrating an oxygen-quenchable luminescent sensor. The Stevens device, designed for use outside the body, includes an oxygen-sensitive luminescent sensor made of pyrene and, disposed adjacent thereto, an oxygen-insensitive reference sensor also made of pyrene but which is covered with an oxygen-impermeable layer. The oxygen concentration is evaluated by comparing the outputs of the measuring and reference sensors.

A principal disadvantage of the prior art sensors is their large size which prohibits their use in the narrow blood vessels, such as the narrow vessels of the heart or those of neonates.

Another disadvantage with the prior art oxygen sensors is that the detected luminescence signal includes a great deal of background noise in addition to the oxygen-quenched luminescence. The noise consists of reflections of the incident signal and broadband luminescence generated by other components in the system, such as the optical fiber. It would be desirable to eliminate the background noise in order to obtain a more precise measurement of oxygen concentration.

An optical system for excitation of a temperature dependent phosphor with radiation and for detecting independent emissions therefrom in first and second wavelength ranges that give an indication of the temperature of the phosphor is disclosed in U.S. Pat. No. 4,459,044 to Alves. The disclosed system includes a light source which transmits light along an optical fiber and a pair of detectors for detecting the emission from the phosphor. However, the system operates in a continuous mode. As a result, the detectors receive the excitation signal as well as the emission from the phosphor and low noise operation is not achieved.

U.S. Pat. No. 3,971,941, issued July 27, 1976 to Sewell et al discloses a radiation detecting system for viewing and imaging wherein infrared radiation is converted to shorter wavelength radiation while preserving the spatial information of the target input. The disclosed system utilizes a gateable detector for temporal discrimination to eliminate the influence of short-term emissions from the quantum mechanical substance.

It is a general object of the present invention to provide an excitation and detection apparatus for use with a sensor comprising a phosphorescent material.

It is a further object of the present invention to provide excitation and detection apparatus for coupling signals to and from a sensor through an optical fiber.

It is yet another object of the present invention to provide excitation and detection apparatus for use with a sensor which emits long-lived luminescence including a measuring wavelength and a reference wavelength.

It is yet another object of the present invention to provide excitation and detection apparatus for use with an oxygen sensor comprising an oxygen-quenchable lanthanide complex.

It is still another object of the present invention to provide excitation and detection apparatus for use with a remotely located phosphorescent material wherein the detector is inhibited during a pulsed excitation signal to achieve low noise operation.

SUMMARY OF THE INVENTION

According to the present invention, these and other objects and advantages are achieved in apparatus for excitation and detection of luminescence comprising a phosphorescent material which emits a relatively long-lived luminescence when exposed to energy in a predetermined wavelength range, source means coupled to the phosphorescent material for generating an incident pulsed energy signal within the predetermined wavelength range to cause the phosphorescent material to generate the long-lived luminescence and detector means coupled to the phosphorescent material for selectively detecting the long-lived luminescence from the phosphorescent material when the incident pulsed energy signal and any relatively short-lived background luminescence generated in the apparatus have substantially ceased. The apparatus preferably includes an optical fiber for coupling the incident pulsed energy signal from the source means to the phosphorescent material and for coupling the long-lived luminescence from the phosphorescent material to the detector means. The phosphorescent material is located at one end of the fiber, and the source means and the detector means are coupled to the other end of the optical fiber along a common optical path.

According to one aspect of the invention, the long-lived luminescence emitted by the phosphorescent material includes a first measuring wavelength and a second reference wavelength and the detector means includes a first detector channel for detecting the first wavelength and a second detector channel for detecting the second wavelength. The first detector channel includes a first optical filter for selecting the first wavelength from the long-lived luminescence and passing it to a first photodetector means for converting the first wavelength to a first signal. The second detector channel includes a second optical filter for selecting the second wavelength from the long-lived luminescence and passing it to a second photodetector means for converting the second wavelength to a second signal. Each detector channel further includes circuit means for storing the respective first and second signals when the incident pulsed energy signal has substantially ceased. Each circuit means includes first integrator means for storing the respective first and second signals and gating means for coupling the respective first and second signals to the integrator means when the source means is off. Preferably, the circuit means each include means for averaging the first and second signals over multiple incident pulsed energy signals. The averaged signals are converted to digital form and processed in a computer.

According to an important aspect of the present invention, the detector means is enabled only when the incident pulsed energy signal from the source means and any relatively short-lived background luminescence generated in the apparatus have substantially ceased. The selective enabling is accomplished by inhibiting the detector means when the source means is on. The detector means effectively detects the desired long-lived luminescence which decays relatively slowly after application of an incident pulsed energy signal and discriminates against the relatively large amplitude incident pulsed energy signal and associated short-lived background luminescence. As a result, a low-noise detection apparatus is provided.

According to another aspect of the invention, the source means includes a broadband light source, a source filter for providing an incident pulsed energy signal within the predetermined wavelength, and a source lens for collimating the output of the light source. The apparatus further includes beam splitter means positioned in the optical path for directing the pulsed energy signal from the light source to the optical fiber and for directing the long-lived luminescence from the optical fiber to the detector means and alignment means for varying the orientation of the beam splitter relative to the axis of the optical fiber to permit alignment of the pulsed incident energy signal with the optical fiber. The alignment means preferably comprises adjustable mounting means for the beam splitter, the mounting means including means for rotating the beam splitter about two perpendicular axes.

According to a further aspect of the invention, the apparatus includes calibration source means for supplying a first calibration signal at the first wavelength to the first detector channel and a second calibration signal at the second wavelength to the second detector channel for calibration of the first and second detector channels. The calibration source means preferably includes a calibration light source for providing the first and second calibration signals and control means for controlling the calibration light source to provide the first and second calibration signals within predetermined intensity limits. In a preferred embodiment, the calibration source comprises a first light emitting diode for providing the first calibration signal and a second light emitting diode for providing the second calibration signal. The calibration source means is preferably located in the same housing as the first and second detector channels.

According to still another aspect of the present invention, the apparatus includes means for detecting spurious signals received on the optical fiber. A movable shutter selectively blocks the optical path between the optical fiber and the detector means. The source means is deenergized and detected signals, with and without the shutter blocking the optical fiber, are compared. When the detected signal in the unblocked condition is greater than the detected signal in the blocked condition, a spurious signal is indicated.

BRIEF DESCRIPTION OF THE DRAWINGS

For a better understanding of the present invention together with other and further objects, advantages and capabilities thereof, reference is made to the accompanying drawings which are incorporated herein by reference and in which:

FIG. 3 is a fragmented illustration of a catheter embodying the fiber optic sensor;

FIG. 4 is a cross-sectional view taken along section lines 4—4 of FIG. 3 showing the catheter lumens;

FIG. 5 is a cross-sectional view taken along section lines 5—5 of FIG. 3 showing the distal end of the catheter;

DETAILED DESCRIPTION OF THE INVENTION

Figure 1:
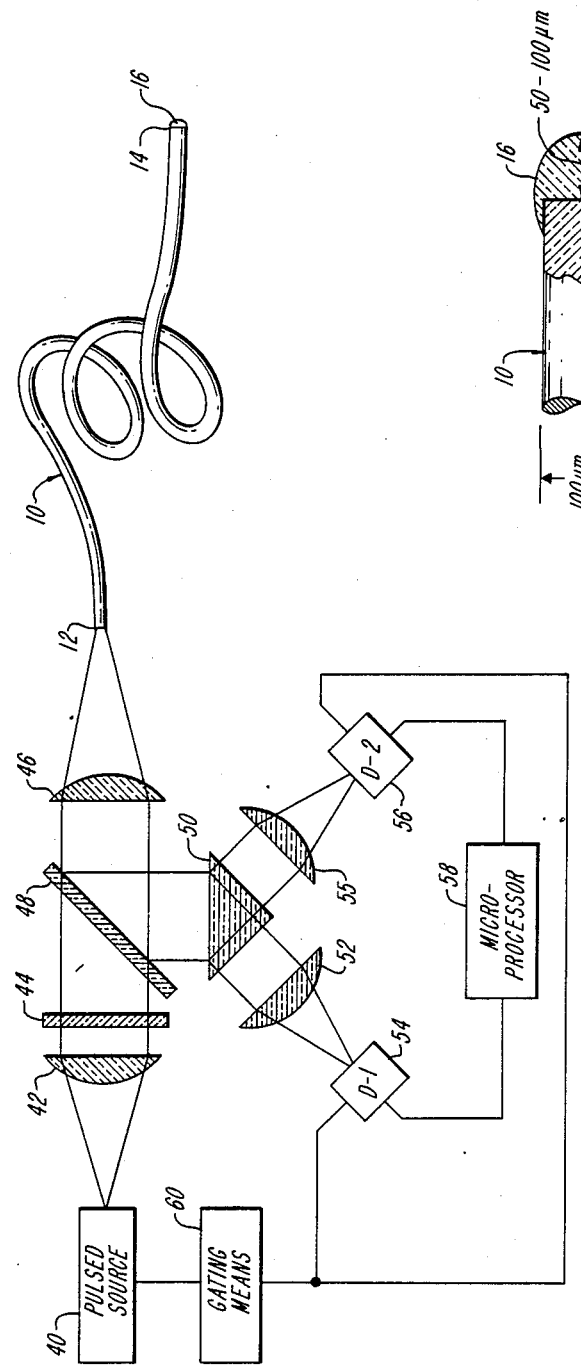
FIG. 1 is a schematic illustration of a fiber optic sensor and associated excitation and detection apparatus in accordance with the present invention.

A sensor system in accordance with the present invention includes a sensor positioned at one end of an optical fiber and excitation and detection apparatus located at the other end of the fiber. The sensor carried by the optical fiber is intended for use within the human body, for example, in a blood vessel, but is not limited to such use. The sensor measures a desired parameter such as the oxygen concentration in blood. Typically, the sensor is a phosphorescent material which emits a long-lived luminescence in response to excitation by an incident pulsed energy signal within a predetermined wavelength range. The characteristics of the phosphorescent material are selected so that the intensity of the long-lived luminescence is varied in response to the parameter being sensed. A phosphorescent material for sensing oxygen concentration is described in detail hereinafter.

The excitation and detection apparatus located at the opposite end of the optical fiber contains two major components; a source subsystem for providing the incident pulsed energy signal to the phosphorescent material through the optical fiber to stimulate emission of the long-lived luminescence, and a detection subsystem for detecting the long-lived luminescence emitted by the phosphorescent material and transmitted through the optical fiber. The detected signal corresponding to the long-lived luminescence is processed and is converted to a measurement of the desired parameter. The excitation and detection apparatus also preferably includes means for calibrating the detection subsystem and means for detecting spurious light signals on the optical fiber.

In an important feature of the present invention, the detection subsystem is inhibited when the light source in the source subsystem is on, thereby eliminating the incident pulsed energy signal and any relatively short-lived background luminescence from the detected signal. The long-lived luminescence is detected during the periods between excitation pulses without interference from the relatively high intensity incident pulsed energy signal. The detection subsystem further includes means for averaging the measured signal over a selected time period to improve accuracy and average out noise which may affect a single pulse measurement. The excitation and detection apparatus is described in detail hereinafter. It will be understood that a variety of different phosphorescent materials can be utilized with the excitation and detection apparatus for sensing a variety of parameters.

In another aspect, this invention consists of a combination measuring and reference sensor containing both quenchable and nonquenchable luminescent materials. A first measuring material has a luminescence in a first wavelength range which is quenched by the analyte. A second reference material is disposed adjacent to the first material and has a luminescence in a second wavelength range different from the first wavelength range and which is not substantially quenched by the analyte. The luminescence from the first material constitutes a measuring signal which is inversely proportional to the concentration of the analyte exposed to the sensor. The luminescence from the second material constitutes a reference signal which is not effected by the presence of the analyte and which is used to continuously monitor the source radiation used to excite the first and second materials and the losses in the sensor system. Because the luminescence from the first and second materials are in different wavelength ranges, a single optical fiber can be used for conducting both of these signals and filter means are used for discriminating the same.

By way of example, the oxygen-quenchable Tb(SALAPPD) complex as a first material and the nonoxygen-quenchable Eu(SALAPPD) complex as the second material are disposed in solid solution in a polymeric matrix. The matrix is disposed at the distal tip of a single optical fiber. The fiber tip is placed in the sample, and the $O_2$ gas in the sample permeates the polymeric matrix. An incident energy signal for exciting both the first and second materials is sent down the fiber and causes the first and second materials to luminesce. The luminescence from the oxygen sensitive terbium complex is reduced in proportion to the concentration of oxygen present whereas the luminescence from the europium complex is proportional to the incident signal, minus any system losses. The luminescence signals from the terbium and europium complexes return down the fiber to its proximal end where they are discriminated by means of filters and sent to separate detectors for measuring the same. The combination sensor will be further described hereinafter with respect to a specific embodiment of a blood gas sensor.

In a third aspect of this invention, a low-noise, phosphorescent analyte sensor is provided. The sensor employs an analyte-quenchable luminescent material having a relatively long-lived luminescence or phosphorescence. A delayed detection of that phosphorescence, after the exciting source energy and any broadband background luminescence has ceased, produces a low-noise output signal. The low-noise sensor will be described by means of a specific embodiment consisting of a fiber optic oxygen sensor probe for in vivo monitoring of the oxygen concentration within a body cavity, such as the blood vessels. The probe will further encompass the first and second aspects of this invention and thus include an oxygen-quenchable luminescent lanthanide complex as the measuring material in combination with a nonoxygen-quenchable luminescent lanthanide complex as a reference material. Both complexes are contained in a polymeric bead disposed at the distal end of a single optical fiber. Both complexes exhibit relatively long-lived luminescence or phosphorescence such that by pulsing an excitation source and selectively coupling and decoupling the detector so that the detector is on only when the excitation source is off and any short-lived background luminscence has ceased, the output signal consists only of the phosphorescent measuring and reference signals.

In order to produce a low-noise measuring and reference signal, the measuring and reference complexes must generate a long-lived luminescence or phosphorescence. As used herein, the term phosphorescence means a relatively long-lived luminescence which exists after the excitation energy has ended, as opposed to short-lived fluorescence which usually ceases in less than $10^{-7}$ seconds when the exciting energy is turned off. Preferably, the phosphorescence has a life-time of at least about $10^{-5}$ seconds, and more preferably greater than about $10^{-4}$ seconds.

The preferred in vivo oxygen probe and associated apparatus are shown in FIGS. 1–5. The sensor includes an optical fiber 10 having a proximal end 12 and a distal end 14. Disposed at the distal end of the fiber is a sensor body 16 consisting of a solid body of a polymeric material containing both the measuring oxygen-quenchable luminescent lanthanide complex and the reference nonoxygen-quenchable luminescent lanthanide complex. Preferably, the polymeric material is poly(methylmethacrylate) which will adhere directly to the fiber. Alternatively, the lanthanide complexes may be adsorbed on porous poly(styrene)/divinylbenzene beads which are dispersed in a silicone elastomer that is directly adhered to the distal end of the fiber, or the porous poly(styrene)/divinylbenzene beads on which the lanthanide complexes are adsorbed may be encapsulated by a porous polyethylene or Teflon sheath, such as Celgard or Goretex, and the sheath attached to the fiber with adhesive.

Figure 2:
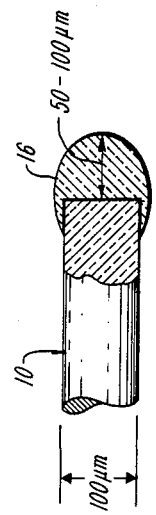
FIG. 2 is a partial cross-sectional view of the distal end of the fiber optic sensor.

The sensor body 16 is preferably formed by dipping the distal end of the fiber in a solution of the polymeric matrix material, the oxygen-quenchable lanthanide complex, and the nonoxygen-quenchable reference complex, and allowing the solvent to evaporate. A small polymeric bead of about 50–100 micrometers can thus be formed on a 100 micrometer diameter fiber, as shown in FIG. 2.

For example, the dipping solution may comprise about 2.5 g of the Tb(SALAPPD) complex, 0.5 g of the Eu(SALAPPD) complex, and 97.0 g of poly(methylmethacrylate) dissolved in ethyl acetate at about 20% solids. The resulting body will thus have about 2.5% by weight of the terbium complex and 0.5% by weight of the europium complex.

To the left of the fiber in FIG. 1, a radiation source, detectors, and various optical and electronic elements are provided. A pulsed incoherent energy source 40, such as a mercury or xenon discharge lamp, produces broadband radiation which is partially collected and collimated by a lens 42. The collimated signal from lens 42 is received by a narrowband filter 44 which rejects nearly all of the radiation from the source except for a narrow segment which includes at least part of a predetermined wavelength range at which the measuring and reference luminescent materials are excited. This narrowband signal is imaged onto the face of the proximal end 12 of the fiber by a second lens 46. The radiation travels to the distal end of the fiber where it passes directly into the gas-absorbing region defined by the body 16. The luminescent radiation generated in the body by the measuring and reference materials is transmitted back through the fiber and lens 46 through a half-silvered mirror 48 to a beam splitter 50 which separates the output radiation into two equal components. The first output component is sent through a filter 52 which passes radiation in the wavelength range of the luminescence from the measuring material and then onto the active area of a first detector 54. The second component of the output signal passes through a filter 55 which passes radiation in the wavelength range of the luminescence of the reference material and finally onto the active area of a second detector 56. The intensities of the luminescence from the measuring and reference materials are thus separately measured and sent to a microprocessor 58 for calculating the value of the oxygen concentration in the blood.

In order to eliminate background noise from the output luminescence signal, a gating means 60 is provided between the source means 40 and the detectors 54 and 56, to selectively couple and decouple the detectors. For example, at a time $t_0$ the gating means sends an electronic signal to the source causing the source to emit a pulse of radiation. At the same time $t_0$ the gating means sends electronic signals to each of the detectors disabling the same. At a predetermined time period after the source means is shut off and any short-lived background luminescence has ceased, the gating means sends a signal to each of the detectors activating the same. In this manner, only the long-lived luminescence from the measuring and reference materials is detected. Other types of gating means may also be used.

The fiber optic sensor is inserted into a blood vessel or body cavity via a carrier means. By carrier means it is meant a flexible or rigid tubular member for insertion into the body vessels or cavities, such as a catheter, needle or probe. A suitable carrier means is shown in FIGS. 3-5, consisting of a catheter formed from an elongate flexible body 102 and which may, for example, be extruded from an appropriate plastic material such as polyurethane or polyvinyl chloride. A 3.5 French catheter, having an outer diameter of 0.045 inch, may be used. The body 102 has a first smaller lumen 104 in which a single optical fiber 110 of the sensor is enclosed, and a second larger lumen 106 for fluid infusion.

The proximal end of the catheter includes a molded fitting 120 which is secured to the catheter body 102. Projecting from the proximal end of the fitting 120 are a pair of flexible tubes 122, 124. The tube 122 is adapted to receive the optical fiber 110, which extends through the fitting 120. The proximal end of the tube 122 is provided with a connector 126 which is connected to the proximal end of the optical fiber 110. Connector 126 is adapted to be mounted with respect to a source of radiant energy, such as a flash lamp (illustrated diagramatically at 127) so that the proximal end of the optical fiber 110 may receive the radiant energy and conduct it along its length to the distal end of the fiber.

The smaller lumen 104 is skived back from the distal end of the catheter body 102, so that the larger lumen 106 extends distally beyond the distal end of the smaller lumen. The optical fiber 110 and sensor body 116 extend slightly beyond the distal end of the smaller lumen so that the sensor tip 116 will be in contact with the blood. The longer wall of the larger lumen helps protect the exposed sensor tip and fiber from breakage. Epoxy 117 is disposed around the fiber between the fiber and smaller lumen adjacent the distal end of the fiber to secure the fiber and sensor in place and to seal the distal end of the smaller lumen.

The other tube 124 at the proximal end of the catheter communicates through the fitting 120 with the larger lumen 106 and preferably is provided with a conventional luer connector 128. The pathway thus defined between the luer connector 128, tube 124, and larger lumen 106 which is open at its distal end permits communication with the region of the patient's blood vessel or body cavity where the distal end of the catheter is located. It provides a passageway for fluids to flow both to and from the patient's blood vessel and also provides a means for making pressure measurements.

More particularly, the preferred in vivo probe for measuring the oxygen concentration of the blood will now be described having a sensor body consisting of the Tb(SALAPPD) complex and Eu(SALAPPD) complex as the measuring and reference materials, respectively, dispersed in a poly(methylmethacrylate) matrix. Both complexes have a maximum excitation efficiency at 350-360 nm, and thus a filter 44 having a bandpass of 350-400 nm is selected The 546 nm emission peak for the terbium complex, and the 616 nm emission peak for the europium complex, are selected for maximum intensity and minimum overlap. A 546±10 nm filter 52 is used for the terbium peak and a 616±10 nm filter 55 is used for the europium peak. The output from the 546 nm filter is substantially 100% terbium. The output of the 616 nm filter is about 95% europium, with the remaining 5% coming from a 623 nm emission peak of terbium. Photomultiplier tubes are used as the detectors 54 and 56.

The optical fiber is a commercially available silica fiber sold under the trademark HCS, by Ensign-Bickford Optical Co., Avon, Connecticut. The pulsed source is a xenon flash lamp, EG&G FX-236, sold by E. G. & G., Salem, Massachusetts, having a pulse width (full width at half maximum amplitude) of 10 microseconds. The Tb(SALAPPD) complex disposed in poly(methyl-methacrylate) has an unquenched lifetime of approximately 1300 microseconds, and the Eu(SALAPPD) complex disposed in poly(methylmethacrylate) has an unquenched lifetime of approximately 550 microseconds. The detectors are gated on about 100 microseconds after the source is shut off which is sufficient for substantially all of the excitation energy and any short-lived luminescence generated in the system to cease.

Figure 6:
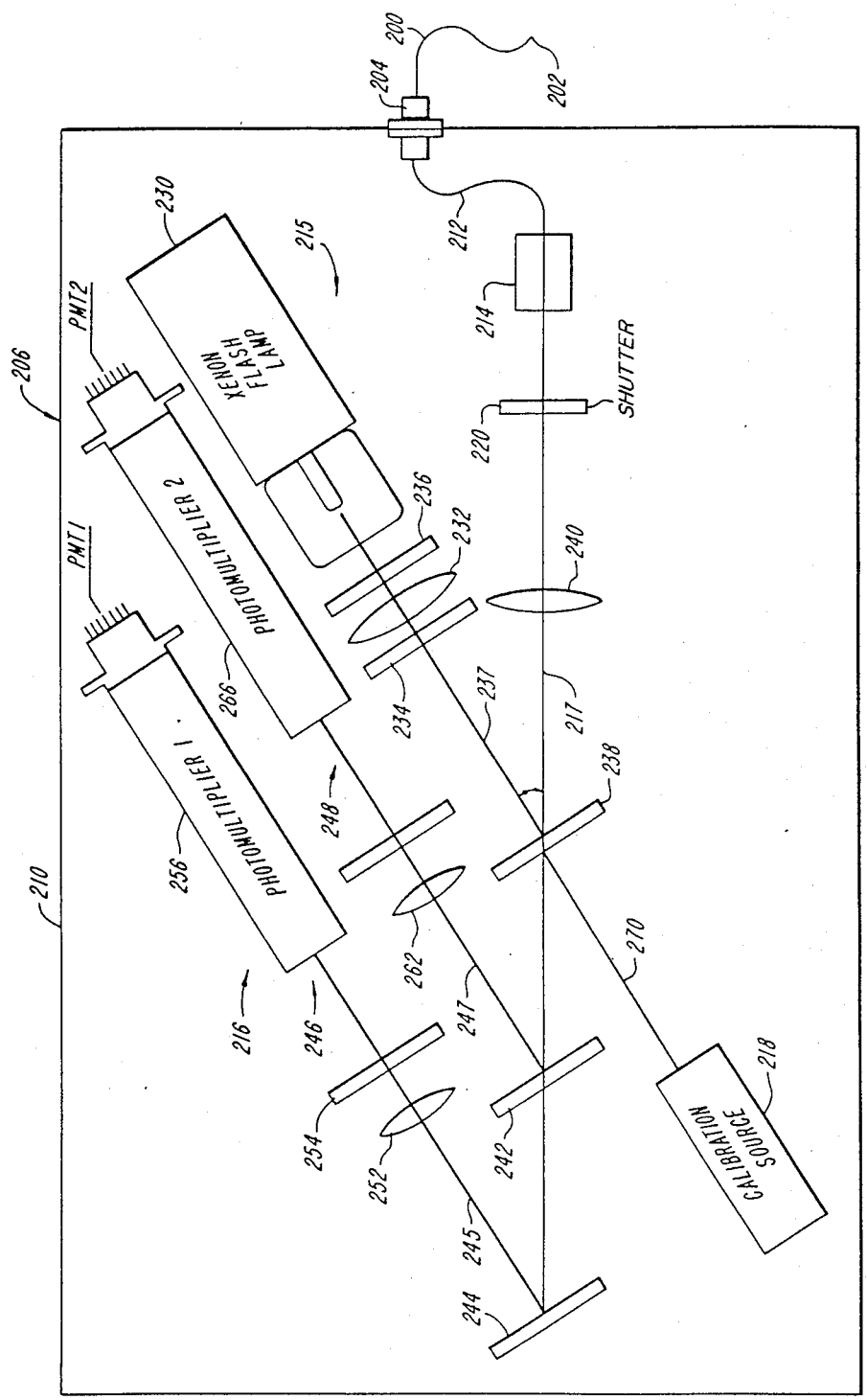
FIG. 6 is a schematic block diagram of the optical portion of a preferred excitation and detection apparatus in accordance with the present invention.
Figure 7:
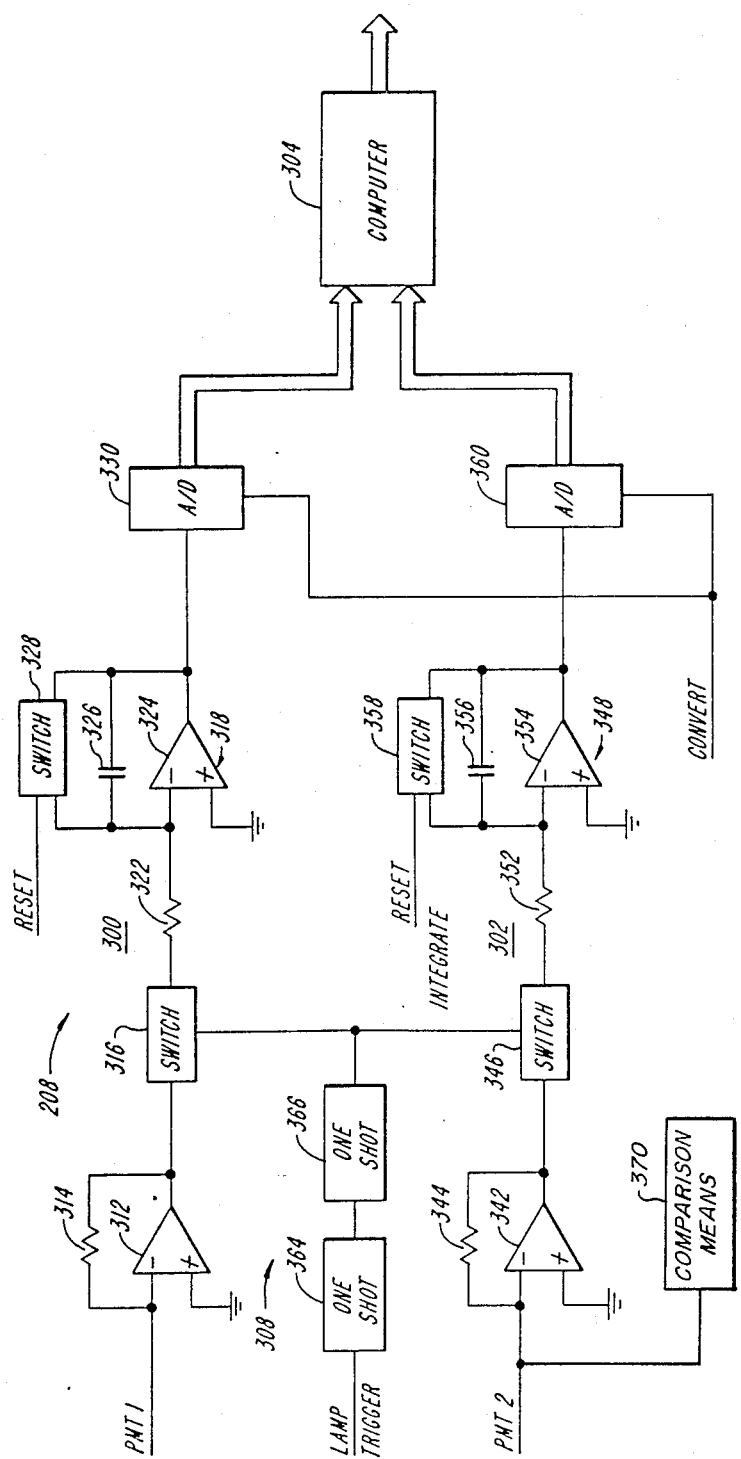
FIG. 7 is a schematic block diagram of circuitry associated with the excitation and detection apparatus shown in FIG. 6.

A preferred embodiment of the apparatus for excitation and detection of luminescence from the phosphorescent material is illustrated in FIGS. 6-10. An optical fiber 200, having a phosphorescent material 202 disposed at its distal end, is connected at its proximal end by means of an optical connector 204 to an excitation and detection apparatus which includes an optical assembly 206 (FIG. 6) and detection circuitry 208 (FIG. 7). The optical assembly 206 is typically contained in a metal housing 210, while the detection circuitry 208 is conveniently mounted on a printed circuit board (not shown).

In the optical assembly 206 of the excitation and detection apparatus, optical fiber 200 is coupled by optical connector 204 to a short length of optical fiber 212. The opposite end of optical fiber 212 is mounted in a housing 214 which holds the fiber 212 in a fixed position so that optical signals may be coupled to and from it. The optical assembly 206 includes a source means 215 for coupling an incident pulsed energy signal through optical fiber 200 to phosphorescent material 202 and a detector means 216 for detecting long-lived emissions from phosphorescent material 202 that are transmitted through optical fiber 200. The source means 215 and the detector means 216 are both coupled to optical fibers 200, 212 along a common optical path 217. The optical assembly 206 is further provided with a calibration source 218, coupled to the common optical path 217, and a shutter 220 for selectively blocking the common optical path 217 near the entrance to optical fiber 212.

The source means 215 preferably includes a xenon flashlamp 230 which has a broadband light output and which is operated in a pulsed mode. Typically, the flashlamp 230 has a 10 microsecond pulse duration and is operated at a repetition rate of about 100 pulses per second. Its output is collimated by a short focal length lens 232 and is filtered by filters 234, 236 to pass a near ultraviolet band of wavelengths between 360 and 390 nanometers. The filters 234 and 236 include a lowpass filter and a highpass filter which together provide a bandpass characteristic. Alternatively, a single bandpass filter of suitable characteristics can be utilized. An ultraviolet pulsed excitation beam 237 supplied through filters 234, 236 and lens 232 is directed onto the common optical path 217 by a beam splitter 238 which is preferably positioned with a normal to its surface oriented at an angle of 30 degrees to the common optical path 217. A lens 240 images the source 230 onto the end of optical fiber 212 in housing 214. The incident pulsed energy signal from the flashlamp 230 is then coupled through optical fiber 212, optical connector 204 and optical fiber 200 to the remotely-located phosphorescent material 202, causing excitation of the phosphorescent material 202 and emission of long-lived luminescence.

The optical part of the detector means 216 is illustrated in FIG. 6. Long-lived luminescence from the phosphorescent material 202 passes as a signal beam through optical fibers 200 and 212 onto common optical path 217. The signal beam passes through lens 240 and impinges on beam splitter 238. Part of the signal beam passes through beam splitter 238 and impinges on a beam splitter 242. A first portion of the signal beam passes through beam splitter 242 and is reflected by a mirror 244 as a signal beam 245 to a first detector channel 246. A second portion of the signal beam is reflected by beam splitter 242 as a signal beam 247 to a second detector channel 248. First detector channel 246 detects the portion of the long-lived luminescence from phosphorescent material 202 in a first wavelength range, while second detector channel 248 detects the portion of the long-lived luminescence in a second wavelength range. In the preferred embodiment of the oxygen sensor described herein, the first detector channel 246 detects emission of the phosphorescent material 202 in a wavelength range centered on 546 nanometers, while second detector channel 248 detects emissions in a wavelength range centered on 616 nanometers.

In the first detector channel 246, the signal beam 245 is coupled through a lens 252 and a narrow band interference filter 254 to a photomultiplier tube 256. The lens 252 focuses the signal beam 245 on a light sensitive surface of the photomultiplier tube 256, while the interference filter 254 selects the desired wavelength from the signal beam 245 for transmission to photomultiplier tube 256. An output signal PMT1 from photomultiplier tube 256 represents the intensity of the long-lived luminescence from phosphorescent material 202 in the wavelength selected by filter 254. Signal PMT1 is supplied to detection circuitry 208 as described hereinafter. In second detector channel 248, the signal beam 247 passes through a lens 262 and a narrow band interference filter 264 to a second photomultiplier tube 266. The lens 262 focuses signal beam 247 on a photosensitive surface of photomultiplier tube 266, while interference filter 264 selects the desired wavelength from signal beam 247 for transmission to photomultiplier tube 266. An output signal PMT2 from photomultiplier tube 266 is supplied to detection circuitry 208 as described hereinafter. Each photomultiplier tube 256, 266 is supplied with appropriate operating voltages from a power supply (not shown).

Calibration source 218 directs a calibration beam 270 at beam splitter 238. The calibration source 218 is energized only when calibration is desired. The calibration beam 270 when energized is reflected by beam splitter 238 along common optical path 217 to beam splitter 242 where it is divided into two beam portions which are directed to first detector channel 246 and second detector channel 248. The calibration beam 270 includes calibration signals at the first and second detection wavelengths of predetermined intensity so that detector channels 246, 248 can be calibrated on a periodic basis to insure accurate operation. The construction of the calibration source 218 is described hereinafter.

Figure 8:
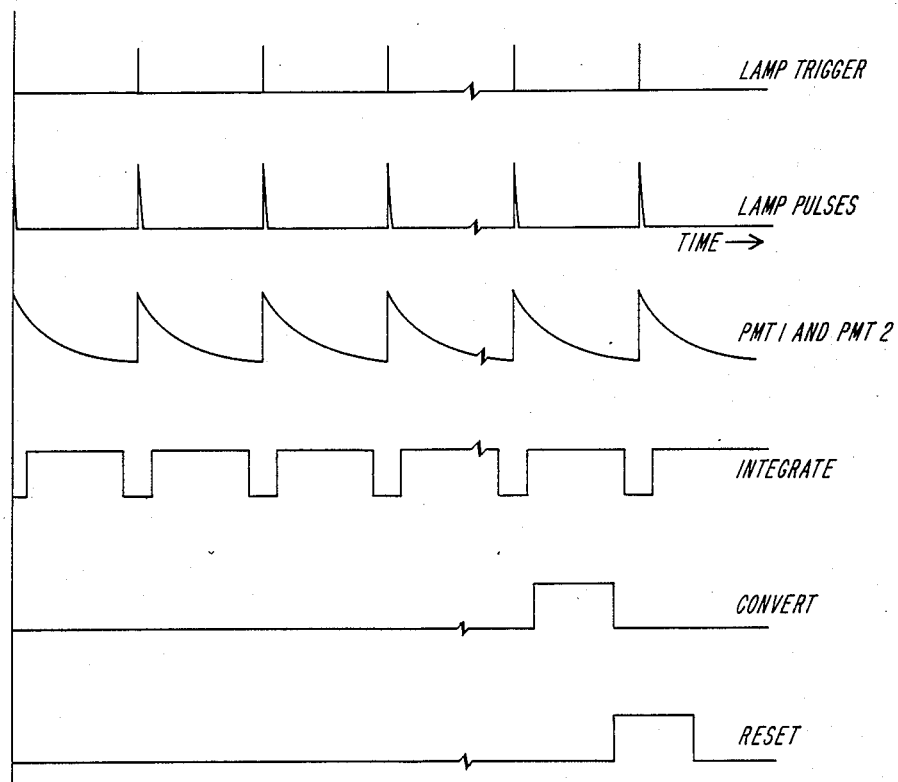
FIG. 8 is a timing diagram illustrating various waveforms in the circuit of FIG. 7.

The detection circuitry 208 is shown schematically in FIG. 7. Waveforms associated with the detection circuitry 208 are illustrated in FIG. 8. The circuitry 208 includes first channel processing circuitry 300 and second channel processing circuitry 302, each of which supply digital signals to a computer 304. The computer 304 processes the signals from each channel and provides a sensor measurement to an numeric display, a printer, display screen or other output device. The detection circuitry 208 further includes timing circuitry 308 for timing the signal processing in each processing channel 300, 302.

The PMT1 signal is supplied to the inverting input of a preamplifier 312. A feedback resistor 314 is connected between the output and the inverting input of preamplifier 312. The output of preamplifier 312 is supplied through an electronically controlled analog switch 316 to the input of an integrator 318. Analog switch 316 is controlled by an INTEGRATE signal on line 320 as described hereinafter. Integrator 318 includes an input resistor 322 connected to the inverting input of an amplifier 324. An integrating capacitor 326 is connected between the inverting input and the output of amplifier 324, and an analog switch 328 is connected in parallel with integrating capacitor 326. The output of amplifier 324 is coupled to the analog input of an analog-to-digital convertor 330 which has its digital outputs coupled to the input of computer 304.

In second channel processor circuit 302, the PMT2 signal is supplied to the inverting input of a preamplifier 342. A feedback resistor 344 is coupled between the inverting input and the output of preamplifier 342. The output of preamplifier 342 is connected through an analog switch 346 to the input of an integrator 348. Analog switch 346 is controlled by the INTEGRATE signal on line 320. Integrator 348 includes an input resistor 352 coupled to the inverting input of an amplifier 354 and an integrating capacitor 356 coupled between the inverting input and the output of amplifier 354. An analog switch 358 is coupled in parallel with integrating capacitor 356. The output of integrator 348 is coupled to the analog input of an analog-to-digital converter 360. The digital outputs of converter 360 are coupled to computer 304.

The timing circuit 308 includes a one-shot timing circuit 364 which is triggered by a LAMP TRIGGER signal and supplies a pulse of predetermined length to a second one-shot timing circuit 366. The one-shot 366 is triggered by the end of the pulse from one-shot 364. As a result, the output from one-shot 366 is delayed from the LAMP TRIGGER signal by the duration of the pulse from one-shot 364. The output of one-shot 366 is the INTEGRATE signal on line 320 which enables analog switches 316, 346. A RESET signal coupled to analog switches 328, 358 causes integrating capacitors 326, 356 to be discharged. A CONVERT signal supplied to analog-to-digital converters 330, 360 causes conversion of the analog value at each input to a digital representation thereof.

Normal operation of the excitation and detection apparatus illustrated in FIGS. 6 and 7 is described with reference to FIG. 8. The xenon flashlamp 230 is triggered with a LAMP TRIGGER signal, as shown in FIG. 8, at a repetition rate of approximately 100 pulses per second. The lamp pulses from flashlamp 230 have a duration of about 10 microseconds. The lamp pulses are filtered by filters 234, 236 to produce the pulsed excitation beam 237 in the ultraviolet band between 360 and 390 nanometers. The pulsed excitation beam 237 is collimated by lens 232, is focused by lens 240 on the end of optical fiber 212 and is transmitted by optical fibers 212 and 220 to the phosphorescent material 202 at the remote end of fiber 200. The phosphorescent material 202 in response to the ultraviolet incident pulsed energy signal emits a long-lived luminescence having a decay time which is long in comparison with the 10 microsecond lamp pulses.

The long-lived luminescence from the phosphorecent material 202 is carried by optical fibers 200, 212 to the optical assembly 206 of the excitation and detection apparatus. The long-lived luminescence travels along the common optical path 217 through beam splitter 238 and is divided by beam splitter 242 into signal beam 245 and signal beam 247. The signal beam 245 is focused by lens 252 on the sensitive area of photomultiplier tube 256 and is filtered by narrow band interference filter 254 to select the 546 nanometer wavelength. Similarly, signal beam 247 is focused by lens 262 on the sensitive surface of photomultiplier 266 and is filtered by narrow band interference filter 264 to select the 616 nanometer wavelength. The ouput signals from the photomultiplier tubes 256, 266 are represented by signals PMT1 and PMT2 in FIG. 8. These signals have waveforms characterized by a fast rise time, which is initiated by the incident energy pulse, and a relatively slow decay time. The two photomultiplier output signals vary independently in amplitude due to intensity variations at the different selected wavelengths.

The LAMP TRIGGER signal shown in FIG. 8 is supplied to one-shot circuit 364 which causes delayed triggering of the one-shot circuit 366, the output of which is the INTEGRATE signal as shown FIG. 8. The duration of the pulse generated by one-shot 364 is selected to be at least as long as the duration of the xenon flashlamp output, which in the present example, is about 10 microseconds. The duration of the pulse generated by one-shot circuit 366 is selected to end before the next LAMP TRIGGER signal occurs. As shown in FIG. 8, the INTEGRATE signal enables analog switches 316 and 346 only during times when xenon flashlamp 230 is off. This insures that the pulsed incident energy signal supplied to the phosphorescent material 202 and any short-lived luminescence associated with the pulsed incident energy signal are not included in the measurements of long-lived luminescence. The time discrimination feature is particularly important because the pulsed incident energy signal is much greater in intensity than the long-lived luminescence from the phosphorescent material 202. As a result, the unwanted signals are removed by the time discrimination and a low noise detector is provided.

The photomultiplier signals PMT1 and PMT2 are amplified by preamplifiers 312 and 342 respectively, and are gated by analog switches 316 and 346, respectively, into integrators 318 and 348 during the times between xenon flashlamp 230 pulses. The signals PMT1 and PMT2 cause charging of integrating capacitors 326 and 356, respectively. The charge stored on each of the capacitors 326, 356 is proportional to the amplitude of the respective signals PMT1 and PMT2 integrated over the time when the respective switches 316 and 346 are enabled. Thus, the output of each integrator 318, 348 is a measure of the time integrated, long-lived luminescence at each selected wavelength.

The integrating capacitors 326 and 356 are discharged by applying the RESET signal to switches 328 and 358, respectively. In accordance with the present invention, there is provided means for averaging the sensed signal over multiple lamp pulses to obtain a more accurate measurement. Averaging is accomplished by permitting capacitors 326, 356 to charge during multiple cycles of the pulsed incident energy signal. Thus, for example, capacitors 326, 356 can be charged for 100 cycles and then reset to repeat the measurement. With reference to FIG. 8, the CONVERT signal is applied to each of the analog-to-digital converters 330, 360 at the end of the integrating and averaging process and prior to the RESET signal which discharges capacitors 326, 356. The integrated and averaged signals are converted to digital form by converters 330, 360 and are supplied to computer 304. The CONVERT and RESET signals can be generated by conventional means such as, for example, by counting LAMP TRIGGER pulses and providing CONVERT and RESET signals when the desired number of pulses has occurred.

The computer 304 can process the digital signals received from converters 330 and 360 in accordance with any desired formula. In one technique, the measured value is determined from the ratio of the intensity at the measuring wavelength to the intensity at the reference wavelength. The computed value can then be supplied to a digital readout (not shown).

According to another aspect of the invention, the excitation and detection apparatus includes means for detecting spurious signals received on the optical fiber 200. Movable shutter 220 selectively blocks the optical path between the optical fiber 200 and the detector means 216. The source means 215 is deenergized, and detected signals with and without the shutter 220 blocking the optical fiber 200 are compared by a comparison means 370 (FIG. 7). When the detected signal in the unblocked condition is greater than the detected signal in the blocked condition, a spurious signal is indicated. Spurious light signals are detected when the detected signals in blocked and unblocked conditions differ by more than a predetermined amount.

Figure 9:
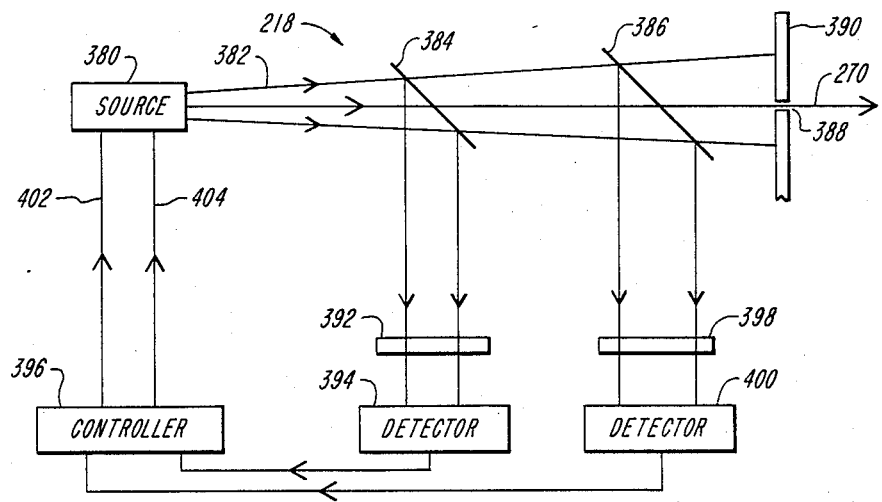
FIG. 9 is a schematic block diagram illustrating the calibration source shown in FIG. 6.

The details of the calibration source 218 are shown in FIG. 9. A light source 380 emits energy in the wavelength bands of the first and second channel detectors 246, 248. In the present example, the source 380 utilizes two independent light emitting diodes (LED's), one transmitting in the green region of the spectrum and having an output at 546 nanometers and the other transmitting in the red region of the spectrum and having an output at 616 nanometers. Two LED chips are mounted on a single substrate to provide the desired dual wavelength output. Such devices are commercially available from Data Display Products, Los Angeles, Calif. Radiation 382 from the source 380 passes through a beam splitter 384, a beam splitter 386 and then passes through a pinhole 388 in an enclosure 390 to form calibration beam 270.

A first portion of the radiation 382 is directed by beam splitter 384 through a narrow band interference filter 392 to a photodetector 394. The output of the detector 394 is supplied to a controller 396. The interference filter 392 preferably has the same passband as interference filter 254 and selects the first wavelength at 546 nanometers for sensing by detector 394. The beam splitter 386 directs a second portion of the radiation 382 through an interference filter 398 to a photodetector 400. The output of photodetector 400 is supplied to controller 396. Interference filter 398 has the same passband as filter 264 and selects the second wavelength at 616 nanometers for sensing by detector 400.

Controller 396 contains circuitry for comparing the outputs of detectors 394, 400, which represent the intensity of the calibration beam 270 at each desired wavelength, with predetermined reference values. In each case, the difference between the measured value and the predetermined reference value is used to generate error signals on lines 402, 404 for increasing or decreasing the current supplied to the LED's which comprise source 380. As a result of the closed loop configuration, each selected wavelength of calibration beam 270 is controlled at the predetermined intensity so that a known calibration signal is provided at each wavelength.

In operation, the calibration beam 270 is directed by beam splitter 238 to the first detector channel 246 and to the second detector channel 248 for verification that the detector channels are operating properly. It will be understood that a variety of factors can affect the output of each detector channel and cause an erroneous reading. Such factors include misalignment of the optical components, foreign material on the optical surfaces which may increase losses and malfunctions of the photomultiplier tubes 256, 266.

Figure 10:
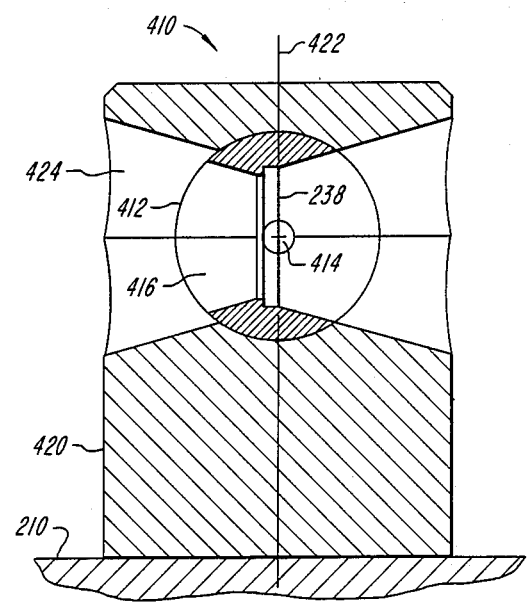
FIG. 10 is a cross-sectional view of an adjustable mounting arrangement for a beam splitter utilized in the apparatus of FIG. 6.

An adjustable mounting device 410 for beam splitter 238 is shown in FIG. 10. The end of optical fiber 212, to which the pulsed incident energy signal from xenon flashlamp 230 is coupled, has a diameter on the order of 0.1 mm. It is, therefore, difficult with a fixed configuration to insure that the focused beam from flashlamp 230 will impinge on the end of optical fiber 212. The focused beam typically has a diameter on the order of 1.5 mm, but is not uniform in intensity, exhibiting the greatest intensity near its center. Accordingly, the apparatus includes means for adjusting the beam from flashlamp 230 so that it is aligned with optical fiber 212. The adjustment means 410 provides a mounting for the beam splitter 238 and permits it to be rotated about two perpendicular axes.

The adjustable device 410 includes a first element 412 having a generally cylindrical shape. Element 412 is rotatable about an axis 414 perpendicular to the paper in FIG. 10. The first element 412 includes a recess for mounting beam splitter 238 and an aperture 416 for passage of light beams to and from beam splitter 238. The first element 412 is mounted for rotation about axis 414 in a cylindrical opening in a second element 420 of generally cylindrical shape and rotatable about an axis 422. The second element 420 is provided with an aperture 424 for passage of light beams to and from beam splitter 238. The base of second element 420 is mounted to housing 210 for rotation about axis 422. The two-cylinder configuration permits the beam splitter 238 to be rotated about two perpendicular axes 414 and 422 during initial alignment of the optical assembly 206. When the light beam from flashlamp 230 is aligned with optical fiber 212, the elements 412 and 420 are locked in position with set screws (not shown).

The following list gives suitable Model Nos. and manufacturers for the elements shown in FIGS. 6 and 7. It will be understood that these are given by way of example only.

| Element | Model No. | Manufacturer |
|---|---|---|
| flashlamp 230 | FX-236 | EG&G |
| photomultiplier tube 256, 266 | R647-01 | Hamamatsu |
| optical filter 234 | UG-5 | Corion |
| optical filter 236 | WG-360 | Corion |
| optical filter 254 | P10-546 | Corion |
| optical filter 264 | P10-616 | Corion |
| beam splitter 238 | P105063 | Esco |
| beam splitter 242 | BS200F | Corion |

-continued

| Element | Model No. | Manufacturer |
|---|---|---|
| lens 232 | A105005 | Esco |
| lens 240 | A105005 | Esco |
| lens 252, 262 | A105010 | Esco |
| preamplifier 312, 342 | HA-5160 | Harris |
| switch 316, 346, 328, 358 | DG212 | Siliconix |
| amplifier 324, 354 | LF412 | National |
| converter 330, 360 | AD573 | Analog Devices |
| computer 304 | 8031 | Intel |
| detector 394, 400 | UV-040BG | EG&G |

Oxygen-quenchable luminescent lanthanide complexes are provided for use as oxygen sensors. The complexes exhibit sufficient oxygen sensitivity in both solid form and in solution for use as oxygen sensors. By complex it is meant a coordination compound formed by the union of a metal ion with a non-metallic ion or molecule called a ligand or complexing agent.

In the lanthanide complexes of this invention, the metal ion is an ion of a lanthanide element. The lanthanide elements, also known as the rare earth elements, consist of those elements having atomic numbers from 57 to 71, and thus include lanthanum, cerium, praseodymium, neodymium, promethium, samarium, europium, gadolinium, terbium, dysprosium, holmium, erbium, thulium, ytterbium, and lutetium. The lanthanide ions which exhibit a narrow-line luminescence are preferred, such as the +3 ions of samarium, europium, dysprosium, terbium, and neodymium.

The lanthanide ions are excited to luminesce by the transfer of energy from at least one ligand which is complexed to one or more lanthanide ions. The ligand absorbs energy to reach an excited singlet state, and may undergo a radiationless transition to an excited triplet state. A transfer of energy from the ligand to the lanthanide ion may occur if the energy of the singlet or triplet states exceeds that of the luminescent state of the lanthanide ion. The oxygen sensitivity of the lanthanide complexes of this invention is believed to result from the creation of a long-lived resonant state between the excited ligand and the excited lanthanide ion of the complex whereby energy is rapidly transferred back and forth between the ligand and ion, and wherein oxygen interferes with the transfer of energy so as to quench the luminescence of the complex.

It has been found that the luminescent lanthanide complexes of this invention are oxygen sensitive when the excited state energy of the ligand is substantially equal to the predetermined excited energy state of the lanthanide ion from which luminescence occurs. When these energies are substantially equal, the ion and ligand form a resonant pair between which energy is rapidly transfered back and forth. Oxygen gas interferes with the energy transfer between the resonant pair or absorbs the energy of the excited ligand to thereby reduce the luminescence intensity. When the excited ligand energy state and the predetermined excited energy state are close enough in energy, the lifetime of the ligand excited state is apparently lengthened through a resonance process with the lanthanide ion excited state. The result is a greater oxygen sensitivity because the oxygen has, in effect, more time in which to interfere with the transfer of energy between the resonant pair or absorb energy from the excited ligand to quench the luminescence.

It has been found that the terbium +3 ion forms oxygen-quenchable complexes with Schiff base ligands. The Schiff base ligand consists of at least one aldehyde or ketone and at least one primary amine. Preferably, the ligand is derived from salicylaldehyde or substituted salicylaldehyde, wherein the substituted salicylaldehyde contains groups other than hydrogen in the 3,4,5, and/or 6 positions. The groups may be halides, hydrocarbons, aldehydes, hydroxides, or any other group. Preferably, the primary amine is selected from the group consisting of 1-amino-2-propanol, 1-amino-2-butanol, 2-amino-1-phenyl-1,2-propanediol, ethylenediamine, and propylenediamine. Preferred Schiff base ligands include:

1:1 salicylaldehyde:1-amino-2-propanol;
1:1 salicylaldehyde:1-amino-2-butanol;
1:1 5-chloro-salicylaldehyde:1-amino-2-propanol;
1:1 3,5-dichloro-salicylaldehyde:1-amino-2-propanol;
1:1 salicylaldehyde:2-amino-1-phenyl-1,2-propanediol;
2:1 salicylaldehyde:ethylenediamine;
2:1 salicylaldehyde:propylenediamine;
1:1 o-vanillin:1-amino-2-propanol; and
1:1 m-vanillin:1-amino-2-propanol.

Known methods for preparing Schiff base complexes can be used, such as those described in U.S. Pat. No. 3,484,380 to Kleinerman.

The terbium +3 ions also forms oxygen-quenchable complexes with $\beta$-diketone ligands. Preferred $\beta$-diketone ligands include:

benzoylacetone;
thenoyltrifluoroacetone;
trifluoroacetylacetone; and
furylbutanedione.

Know methods for preparing $\beta$-diketone complexes can be used, such as those described in R. E. Whan et al., "Luminescent Studies of Rare Earth Complexes: Benzoylacetonate and Dibenzoylmethide Chelates," 8 J. Mol. Spectroscopy 315-327 (1962).

These Schiff base and $\beta$-diketone terbium complexes are excitable by ultra-violet or visible radiation and emit a luminescent radiation at wavelengths longer than the excitation wavelength. All of these complexes can be excited above 300 nm, and preferably are excited at about 350-360 nm.

Furthermore, the lanthanide complexes of this invention can be a ternary (or higher) complex where in addition to a Schiff base and/or $\beta$-diketone ligand, an additional ligand is provided. The additional ligand acts as a filler to complete the coordination geometry and to give a stabler complex. Suitable additional ligands include polyaminocarboxylic acids and heterocyclic polycarboxylic acids such as ethylenediaminetetraacetic acid (EDTA), 1,2-diaminocyclohexane-N,N,N',N'-tetraacetic acid (CyDTA), diethylenetriaminepentaacetic acid (DTPA), ethylene glycol-bis(aminoethyl)-tetraacetic acid (EGTA), and dipicolinic acid (dpa).

It has been found that certain terbium complexes with Schiff base and $\beta$-diketone ligands are oxygen quenchable, while europium complexes with the same ligands are not. The oxygen sensitivity of the terbium complexes is believed to be due to the fact that the excited ligand energy state is substantially equal to the excited energy state of the terbium ion, whereas the excited ligand energy state is not substantially equal to the excited energy state of the europium ion and therefore the europium complex is not oxygen sensitive. By way of example, a preferred oxygen-sensitive terbium complex, hereinafter referred to as Tb(SALAPPD), is formed of three terbium +3 ions, three hydroxides, and three Schiff base ligands of the formula 1:1 salicylaldehyde:2-amino-1-phenyl-1,2-propane-diol (SALAPPD). Each terbium ion has at least two binding sites and thus the ligands are chelates.

The complex is believed to have a closed ring structure with both the ligands and hydroxides acting as bridges. Each ligand is believed to be complexed to two lanthanide metal ions in the ring. The complex is thus a multi-metal complex and it is believed that energy transfer occurs between the various lanthanide metal ions and ligands on the ring. It is further believed that the hydroxide groups may act as bridges between the lanthanide metal ions in the complex.

The terbium ion has a $^5D_4$ excited state at about 490 nm (20,410 cm$^{-1}$). It has been found that the SALAPPD ligand has an excited energy state within about 10 nm (410 cm$^{-1}$) of the $^5D_4$ excited state of the terbium ion. The excited state of the Schiff base ligand is thus sufficiently close to the metal-centered $^5D_4$ excited state of the terbium ion (within about 410 cm or about 2%) so as to produce significant oxygen sensitivity. In contrast, the europium ion has a $^5D_1$ excited state at about 526 nm (19,010 cm$^{-1}$) and a $^5D_0$ excited state at about 570 nm (17,540 cm$^{-}$). The excited state of the Schiff base differs by more than about 20 nm 800 cm$^{-1}$ or about 4%) from either of the $^5D_1$ or $^5D_0$ excited states of the europium ion and it is found that the europium complex is not oxygen sensitive. When the excited ligand state and excited lanthanide ion state are close enough in energy, the complex has oxygen sensitivity. By combining the europium ion with another ligand having an excited ligand energy state sufficiently close to the europium excited state, a europium complex can be made which is oxygen sensitive.

This invention also includes methods for improving the oxygen sensitivity of the lanthanide complexes of this invention. A first process consists of reacting the ligand with a strong base, such as sodium or ammonium hydroxide, to deprotonate the ligand and thus form sites for binding with the metal lanthanide ion. Preferably, the metal lanthanide ion is then added to a solution of the ligand and hydroxide whereby the hydroxide groups form additional ligands to the lanthanide ion. It is believed that the hydroxide groups may coordinate with more than one lanthanide ion and thus act as bridging elements to form a multi-metal ion complex, particularly with the Schiff base ligands. The hydroxide is preferably used at a hydroxide:ligand ratio of 1:1, which results in both deprotonation of the ligand and may result in coordination by hydroxide ligands when the metal ion is added to the solution. Use of a substantially higher concentration of hydroxide is not preferred because it may cause a lanthanide hydroxide to precipitate out.

A second preferred process for making the lanthanide complex consists of a purification step wherein non-oxygen sensitive byproducts are removed. The purification step consists of dissolving the lanthanide complex in a suitable organic solvent, such as chloroform or ethanol, filtering off the insoluble residue (of less oxygen sensitive byproducts), and reprecipitating the compound to produce a more oxygen sensitive complex.

The following two examples set forth specific embodiments of the processes for preparing a Schiff base terbium complex and a $\beta$-diketone terbium complex. Terbium complexes with other preferred Schiff base ligands can be made according to the synthesis described in Example 1 with the substitution of suitable starting materials for the selected ligand.

EXAMPLE 1

Synthesis of Tb(SALAPPD), a Schiff base complex of Tb +3.

The ligand is synthesized by adding 18 mmoles (3.0 g) of (1S, 2S)-(+)-2-amino-phenyl-1,3-propanediol to a solution of 18 mmoles (2.2 g) of salicylaldehyde in 60 ml of absolute ethanol. This solution is placed in an ultrasonic bath at room temperature until the diol has dissolved and a yellow precipitate (SALAPPD) has formed. The solvent is removed by vacuum filtration. The ligand is recrystallized from 175 ml of hot absolute ethanol. The complex is prepared by dissolving 5.5 mmoles (1.50 g) of SALAPPD in 50 ml of 95% ethanol. 2.8 ml of 2M NaOH in aqueous solution are added, and the solution is stirred for several minutes. 1.84 mmoles (0.69 g) of $TbCl_3$ $6H_2O$ are dissolved in 10 ml of 50% ethanol and added to the ligand solution. The yellow precipitate which forms is filtered from the solution and placed in a vacuum desiccator overnight to dry. The dry product is crushed into a powder and dissolved in 10 ml of dry chloroform. After filtration, the solvent is removed by evaporation or under vacuum. The purified product is crushed and desiccated until use.

EXAMPLE 2

Synthesis of Tb(TTFA) into a powder, a $\beta$-diketone complex of Tb +3.

9 mmoles (2.0 g) of thenoyltrifluoroacetone (TTFA) and 3 mmoles (1.12 g) of $TbCl_3$ $6H_2O$ are dissolved in 50 ml of boiling distilled water. 1M aqueous NaOH is added dropwise until formation of the yellow product is complete. The solution remains acidic. After removal of the solvent by filtration, th product is air dried. The metal complex is purified by dissolving in 100 ml of hot absolute ethanol and filtering. Water is added to the ethanol solution to force the complex out of solution. The final product is removed from solution by filtration and the residual solvent is removed by evaporation or under vacuum. The purified product is desiccated until used.

In a preferred embodiment, the oxygen sensor of this invention consists of an oxygen-quenchable lanthanide complex dispersed as a solid solution in a polymeric matrix. The polymer is substantially transparent both to the excitation wavelength and the emission wavelength of the lanthanide complex. The polymeric matrix is permeable to oxygen so as to transfer oxygen from the external fluid (liquid or gas) sample to the lanthanide complex. For example, suitable polymeric materials include poly(styrene), poly(styrene)/-divinylbenzene, poly(methylmethacrylate), and silicone elastomers. Poly(methylmethacrylate) is preferred where the excitation wavelength is in the ultraviolet region, because this polymer is substantially optically transparent to and will not degrade in the presence of UV radiation. A suitable poly(methylmethacrylate) is sold by Polysciences, Inc. of Warrington, Pa., having an intrinsic viscosity of 0.2 and an approximate molecular weight of 33,000. Silicone elastomers containing the terbium complexes are preferably used in a nonaqueous environment because the luminescence response exhibits some degradation in an aqueous environment. However, the terbium complex adsorbed on poly(styrene)/divinylbenzene beads and dispersed in a silicone elastomer produces a stable sensor body which will not substantially degrade in an aqueous environment.

The oxygen sensitivity of a sensor consisting of an oxygen-quenchable lanthanide complex dispersed in a solid polymeric matrix depends upon three factors: (1) the complex; (2) the matrix; and (3) the concentration of the complex in the matrix. Furthermore, the desired sensitivity of the oxygen sensor depends upon the level of oxygen to be measured. One method of evaluating the sensitivity of $O_2$ sensors is to determine the luminescence ratio of a nitrogen saturated sample compared to a sample equilibrated with a known level (usually 20%) of oxygen. This ratio can be used to determine the utility of a test complex at a given concentration in a specific matrix. In an in vivo medical application where the $O_2$ concentration is determined in a substantially aqueous solution, this ratio may range from about 2 to about 15. The previously described preferred Schiff base ligands based on salicylaldehyde or substituted slicylaldehydes fall within this range. The following $\beta$-diketone ligands create terbium complexes which when dispersed in a silicone elastomer also fall within this range: benzoylacetone; trifluoroacetylacetone; and furylbutanedione. The terbium complex of thenoyltrifluoroacetone dispersed in a silicone matrix has a very high intensity ratio (i.e., about 35) which makes it suitable for use at very low oxygen concentrations, below that normally encountered in a medical application. However, by dispersing this complex in poly(methylmethacrylate), which takes up less oxygen than silicone, a less sensitive oxygen sensor can be made. In contrast, other $\beta$-diketone terbium complexes have an intensity ratio of less than two when dispersed in a silicone matrix, e.g., dibenzoylmethane or trifluorophenylbutanedione, and are thus suitable for use at much higher oxygen concentrations.

A modified Stern-Volmer relationship is used to determine the partial pressure of oxygen from the measuring and reference signals. The Stern-Volmer relation at 546±10 nm is a relatively steep line indicating the oxygen sensitivity of the terbium complex. The relationship is defined by the equation:

$$\frac{I_o}{I} = 1 + K_{546}PO_2 \qquad (I)$$

where $I_0$ is the luminescence intensity at 546±10 nm with no oxygen present, I is the luminescence intensity at 546±10 nm in the presence of oxygen, and $K_{546}$ is the Stern-Volmer constant at 546±10 nm.

The Stern-Volmer relation at 616±10 nm is almost a horizontal line representing a very slight oxygen response attributable to the weak terbium luminescence. The relation has the formula:

$$\frac{I_o}{I} = 1 + K_{616}PO_2 \qquad (II)$$

where $I_0$ is a luminescence intensity at 616±10 nm with no oxygen present, I is the luminescence intensity at 616±10 nm with oxygen present, and $K_{616}$ is the Stern-Volmer constant at 616±10 nm.

Combining formulas I and II results in the following relation:

$$\frac{R}{R_o} = \frac{1 + K_{546}PO_2}{1 + K_{616}PO_2} \quad \text{(III)}$$

where $R_o$ is the luminescence intensity at 616±10 nm divided by the luminescence intensity at 546±10 nm with no oxygen present, and R is the intensity at 616±10 nm divided by the intensity at 546±10 nm in the presence of oxygen. Thus, by inserting into formula III the intensity values measured for the terbium and europium complexes at 546 and 616 nm, respectively, and knowing the constants $K_{546}$ and $K_{616}$ determined from initial calibration with known concentrations of $O_2$, the partial pressure of oxygen in the sample can be determined. The use of the reference signal at 616 nm provides continuous monitoring of the level of the incident signal and the losses in the system during use.

The Tb(SALAPDD) complex disposed in a poly(methylmethacrylate) matrix has been found to have a Stern-Volmer constant $K_{546}$ of greater than about $9 \times 10^{-3}$ mm Hg$^{-1}$. The sensitivity of the Tb(TTFA) complex in the same polymeric matrix is even greater. In selecting an oxygen-quenchable lanthanide complex for a specific application, one must balance the sensitivity against the concentration of oxygen to be measured to ensure that a measurable intensity results. The normal ranges of oxygen concentration in the blood are for arterial blood from about 80–100 mm Hg, for venous blood from about 35–45 mm Hg, and for neonatal blood in the umbilical vessel from about 60–80 mm Hg. The preferred sensor, consisting of about 2.5% by weight of the Tb(SALAPPD) complex in poly(methylmethacrylate), allows a determination of $PO_2$ within all three normal blood oxygen ranges to an accuracy of within about ±5%.

While there has been shown and described what is at present considered the preferred embodiments of the present invention, it will be obvious to those skilled in the art that various changes and modifications may be made therein without departing from the scope of the invention as defined by the appended claims.

We claim:

1. Sensing apparatus comprising:
   an optical fiber;
   a phosphorescent material coupled to one end of said optical fiber, said phosphorescent material emitting a long-live luminescence when exposed to energy in a predetermined wavelength range, said long-lived luminescence including a measuring wavelength having an intensity responsive to a quantity being sensed and a reference wavelength having a substantially constant intensity as a function of the quantity being sensed;
   source means coupled to the other end of said optical fiber for generating an incident pulsed energy signal within said predetermined wavelength range to cause said phosphorescent material to generate said long-lived luminescence; and
   detector means coupled to the other end of said optical fiber for selectively detecting the long-lived luminescence from said phosphorescent material when said incident pulsed energy signal has substantially ceased and any short-lived background luminescence generated in the apparatus has substantially ceased, said long-lived luminescence having a longer duration than said incident pulsed energy signal and said short-lived luminescence, said detector means including
   a first detector channel for detecting the measuring wavelength and providing a first signal representative of the intensity of the measuring wavelength,
   a second detector channel for detecting the reference wavelength and providing a second signal representative of the intensity of the reference wavelength,
   signal processing means responsive to the relative values of said first signal and said second signal for providing an output representative of the quantity being sensed, and
   spurious signal detecting means for determining that said detector means is receiving spurious light signals on said optical fiber.

2. Apparatus as defined in claim 1 wherein said spurious signal sensing means includes shutter means for selectively blocking said optical path from said optical fiber and means for comparing the light signals received by said detector means in the blocked and unblocked conditions when said source means is deenergized.

3. Apparatus as defined in claim 2 wherein said shutter means includes a shutter positioned adjacent the other end of said optical fiber and movable to a position where it blocks the optical path between said optical fiber and detector means.

4. Sensing apparatus comprising:
   an optical fiber;
   a phosphorescent material coupled to one end of said optical fiber, said phosphorescent material emitting a long-lived luminescence when exposed to energy in a predetermined wavelength range, said long-lived luminescence including a measuring wavelength having an intensity responsive to a quantity being sensed and a reference wavelength having a substantially constant intensity as a function of the quantity being sensed;
   source means coupled to the other end of said optical fiber for generating an incident pulsed energy signal within said predetermined wavelength range to cause said phosphorescent material to generate said long-lived luminescence;
   detector means coupled to the other end of said optical fiber for selectively detecting the long-lived luminescence from said phosphorescent material when said incident pulsed energy signal has substantially ceased and any short-lived background luminescence generated in the apparatus has substantially ceased, said long-lived luminescence having a longer duration than said incident pulsed energy signal and said short-lived luminescence, said detector means including
   a first detector channel for detecting the measuring wavelength and providing a first signal representative of the intensity of the measuring wavelength,
   a second detector channel for detecting the reference wavelength and providing a second signal representative of the intensity of the reference wavelength, and
   signal processing means responsive to the relative values of said first signal and said second signal for providing an output representative of the quantity being sensed; and
   calibration source means for supplying a first calibration signal at the measuring wavelength to said first detector channel and a second calibration signal at the reference wavelength to said second detector channel for calibration of said first and second detector channels.

5. Sensing apparatus as defined in claim 4 wherein said signal processing means includes first circuit means for integrating said first signal when said incident pulsed energy signal has substantially ceased and second circuit means for integrating said second signal when said incident pulsed energy signal has substantially ceased.

6. Sensing apparatus as defined in claim 5 wherein said first circuit means and said second circuit means include means for integrating said first and second signals, respectively, after multiple incident pulsed energy signals to obtain average values of said first and second signals.

7. Sensing apparatus as defined in claim 4 wherein said first detector channel includes a first photodetector means for converting said measuring wavelength to a first signal and a first optical filter for selecting said measuring wavelength from said long-lived luminescence and passing it to said first photodetector means and said second detector channel includes a second photodetector means for converting said reference wavelength to a second signal and a second optical filter for selecting said reference wavelength from said long-lived luminescence and passing it to said second photodetector means.

8. Sensing apparatus as defined in claim 4 wherein said source means and said detector means are coupled to said optical fiber along a common optical path and further including beam splitter means positioned in said optical path for directing said pulsed energy signal from said source means to said optical fiber and for transmitting said long-lived luminescence from said optical fiber to said detector means and alignment means for varying the orientation of said beam splitter relative to the axis of said optical fiber to permit alignment of said pulsed incident energy signal with said optical fiber.

9. Apparatus as defined in claim 8 wherein said alignment means includes a first element for holding said beam splitter and a second element for holding said first element, said first element being rotatable relative to said second element about a first axis, and said first and second elements being rotable about a second axis, said first and second axes being perpendicular to each other.

10. Apparatus as defined in claim 8 wherein said alignment means comprises adjustable mounting means for said beam splitter, said mounting means including means for rotating said beam splitter about two perpendicular axes.

11. Apparatus as defined in claim 4 wherein said calibration source means includes a calibration light source for providing the first and second calibration signals and control means for controlling said calibration light source to provide said first and second calibration signals within predetermined intensity limits.

12. Apparatus as defined in claim 11 wherein said control means includes means for sensing said first and second calibration signals, means for comparing said calibration signals with respective predetermined intensity limits and means for providing first and second error signals respectively, to said calibration light source when either of said calibration energy signals is outside its respective predetermined intensity limit.

13. Apparatus as defined in claim 12 wherein said calibration source comprises a first light emitting diode providing said first calibration signal and a second light emitting diode providing said second calibration signal.

14. A sensing method comprising the steps of:
stimulating a phosphorescent material with an incident pulsed energy signal within a predetermined wavelength range to cause emission of luminescence including a measuring wavelength having an intensity responsive to a quantity being sensed and a reference wavelength having a substantially constant intensity as a function of the quantity being sensed, the phosphorescent material being stimulated by coupling the incident pulsed energy signal to the phosphorescent material through an optical fiber;
detecting the measuring wavelength and providing a first signal representative of the intensity of the measuring wavelength;
detecting the reference wavelength and providing a second signal representative of the intensity of the reference wavelength, the steps of detecting the measuring wavelength and detecting the reference wavelength including the steps of coupling the luminescence through the optical fiber for detection and discriminating against the incident pulsed energy signal so as to provide low-noise detection of said luminescence;
providing an output representative of the quantity being measured based on the relative values of said first signal and said second signal; and
detecting spurious light signals on said optical fiber by comparing a detected light signal when said optical fiber is blocked with a detected light signal when said optical fiber is unblocked, spurious light signals being detected when the detected signals in blocked and unblocked conditions differ by more than a predetermined amount.

15. A sensing method as defined in claim 14 wherein the step of processing the first signal and the second signal includes the steps of integrating the first signal when said incident pulsed energy signal has substantially ceased and integrating the second signal when said incident pulsed energy signal has substantially ceased.

16. A sensing method as defined in claim 15 wherein the step of processing the first signal and the second signal includes the step of inhibiting the first signal and the second signal from being integrated during said incident pulsed energy signal.

17. A sensing method as defined in claim 16 wherein the step of processing the first signal and the second signal includes repeating the integration of said first signal and said second signal after multiple incident pulsed energy signals so as to obtain average values of said first and second signals.

* * * * *